United States Patent
Shoichet et al.

(10) Patent No.: US 12,343,916 B2
(45) Date of Patent: Jul. 1, 2025

(54) ANTI-ADHESIVE HYDROGEL COMPOSITION

(71) Applicant: THE GOVERNING COUNCIL OF THE UNIVERSITY OF TORONTO, Toronto (CA)

(72) Inventors: Molly Shoichet, York (CA); Michael J. Cooke, Toronto (CA)

(73) Assignee: THE GOVERNING COUNCIL OF THE UNIVERSITY OF TORONTO, Toronto (CA)

(*) Notice: Subject to any disclaimer, the term of this patent is extended or adjusted under 35 U.S.C. 154(b) by 876 days.

(21) Appl. No.: 17/595,471

(22) PCT Filed: May 18, 2020

(86) PCT No.: PCT/CA2020/050667
§ 371 (c)(1),
(2) Date: Nov. 17, 2021

(87) PCT Pub. No.: WO2020/232540
PCT Pub. Date: Nov. 26, 2020

(65) Prior Publication Data
US 2022/0249744 A1 Aug. 11, 2022

Related U.S. Application Data

(60) Provisional application No. 62/849,739, filed on May 17, 2019.

(51) Int. Cl.
C08L 1/28 (2006.01)
A61L 31/04 (2006.01)
(Continued)

(52) U.S. Cl.
CPC ........ *B29C 45/7686* (2013.01); *A61L 31/041* (2013.01); *A61L 31/042* (2013.01);
(Continued)

(58) Field of Classification Search
CPC .... A61P 41/00; C08L 1/28; C08L 5/08; C08L 2203/02
See application file for complete search history.

(56) References Cited

FOREIGN PATENT DOCUMENTS

| CA | 2703807 A1 | 11/2011 |
|----|------------|---------|
| CA | 2705083 A1 | 11/2011 |
| WO | WO 2007/120818 | 10/2007 |

OTHER PUBLICATIONS

Rajfer, Rev. Urol., vol. 7(4), pp. 238-239, publ. 2005 (Year: 2005).*
(Continued)

*Primary Examiner* — Sarah Pihonak
(74) *Attorney, Agent, or Firm* — Norton Rose Fulbright US LLP

(57) ABSTRACT

A method of reducing or limiting tissue adhesion comprises contacting the tissue with an effective amount of a hydrogel composition comprising: 2% to 6% by weight hyaluronan, and 3% to 18% by weight methylcellulose, wherein the combined total amount of hyaluronan and methylcellulose in the hydrogel is between 8 and 24% by weight; and wherein the ratio of hyaluronan:methylcellulose is between 1:1 and 1:5 w/w. The hydrogel composition and may be used to reduce or limit tissue adhesion that is correlated with surgery, and may be used in surgeries wherein the surgery is performed through a small incision or opening.

18 Claims, 3 Drawing Sheets

(51) Int. Cl.
    *A61P 41/00* (2006.01)
    *B29C 45/04* (2006.01)
    *B29C 45/17* (2006.01)
    *B29C 45/76* (2006.01)
    *C08L 5/08* (2006.01)

(52) U.S. Cl.
    CPC ...... *B29C 45/0408* (2013.01); *B29C 45/1756* (2013.01); *C08L 1/28* (2013.01); *C08L 5/08* (2013.01); *B29C 2945/76464* (2013.01); *B29C 2945/76973* (2013.01); *C08L 2203/02* (2013.01)

(56) References Cited

OTHER PUBLICATIONS

Sun et. al., Evidence Based Complem. & Alt. Med., vol. 2014, pp. 1-6 (Year: 2014).*
Extended European Search Report issued in European Patent Application No. 20809328.6, dated May 11, 2023.
Ito et al., "The prevention of peritoneal adhesions by in situ cross-linking hydrogels of hyaluronic acid and cellulose derivatives," Biomaterials, 28(6):975-983, 2006.
International Search Report and Written Opinion for Application No. PCT/CA2020/050667, mailed Jul. 20, 2020, 3 pages.
Ho et al., "A hyaluronan/methylcellulose-based hydrogel for local cell and biomolecule delivery to the central nervous system". Brain Research Bulletin, Mar. 18, 2019 (Mar. 18, 2019), vol. 148, pp. 46-54.
Kang et al. A New Paradigm for Local and Sustained Release of Therapeutic Molecules to the Injured Spinal Cord for Neuroprotection and Tissue Repair, Tissue Engineering: Part A, vol. 14, No. 3, 2009.

* cited by examiner

ANTI-ADHESIVE HYDROGEL COMPOSITION

This application is a national phase application under 35 U.S.C. § 371 of International Application No. PCT/CA2020/050667 filed May 18, 2020, which claims priority from U.S. Application No. 62/849,739 filed May 17, 2019 which are incorporated herein by reference.

TECHNICAL FIELD

This invention relates to anti-adhesive hydrogel compositions and methods of administering hydrogel compositions.

BACKGROUND OF THE ART

Following surgery, tissues can adhere to themselves and/or other tissues. This can cause post-surgical complications such as chronic pain. Anti-adhesive barriers can be applied to limit tissue adhesion; however, current barriers are difficult to deliver and/or do not sufficiently reduce or limit tissue adhesion. Alternative delivery strategies and compositions are needed to improve efficacy of these barriers.

BRIEF SUMMARY

In one embodiment, there is provided a method of reducing or limiting tissue adhesion comprising contacting the tissue with an effective amount of a hydrogel composition that includes: 2% to 6% (or more particularly between 3 and 5%) by weight hyaluronan, and 3% to 18% (or more particularly between 8 and 10%) by weight methylcellulose; the combined total amount of hyaluronan and methylcellulose in the hydrogel being between 8 and 24% (or more particularly between 10 and 16%) by weight and the ratio of hyaluronan to methylcellulose being between 1:1 and 1:5 w/w (or more particularly between 1:1.5 and 1:3 w/w, in one embodiment 1:2.14 w/w.)

In some embodiments, the hydrogel composition consists or consists essentially 2% to 6% (or more particularly between 3 and 5%) by weight hyaluronan, and 3% to 18% (or more particularly between 8 and 10%) by weight methylcellulose; the combined total amount of hyaluronan and methylcellulose in the hydrogel being between 8 and 24% with the remainder of the hydrogel being water and biocompatible buffers and/or salts, which may include disodium hydrogen phosphate, sodium chloride, potassium chloride and/or potassium dihydrogen phosphate.

In one embodiment, the hyaluronan has a molecular weight between 100,000 g/mol and 3,000,000 g/mol and the methylcellulose has a molecular weight between 10,000 g/mol and 500,000 g/mol.

The hydrogel composition may be injectable.

The tissue can be a tissue of the central nervous system, abdominal cavity, or joint.

The hydrogel composition may be administered to a patient during surgery or perioperatively, which surgery may be laparoscopic surgery. Such surgeries include spinal surgery, disc repair surgery, cataract removal surgery, caesarean section, joint replacement or repair, hysterectomy, or dental surgery.

The tissue adhesion can be fibrosis, which may be dural fibrosis or laminectomy fibrosis.

An effective amount can be between 1 and 100 mL.

As demonstrated in the examples, tissue adhesion may be limited for a period of greater than or equal to 1 week, 2 weeks, 3 weeks, 4 weeks, 5 weeks, 6 weeks, 7 weeks or 8 weeks.

Also provided are hydrogel compositions for use in the above methods.

DETAILED DESCRIPTION

Figure 1:
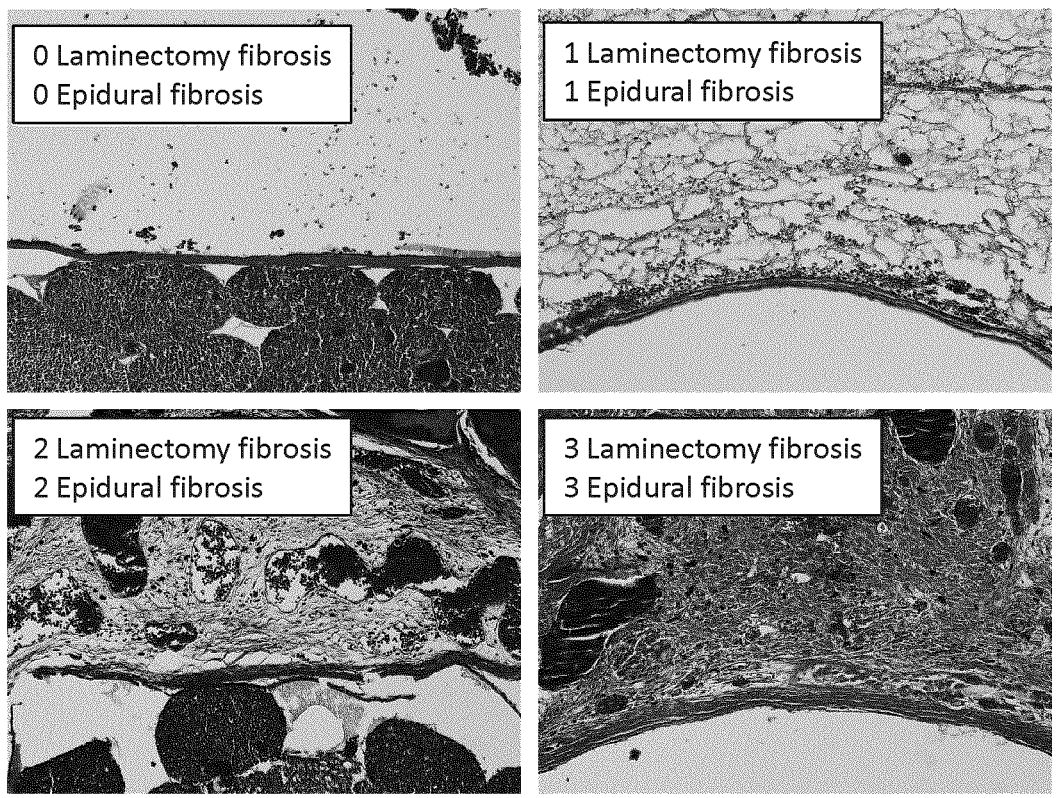
FIG. 1 shows the scoring system used for the level of laminectomy fibrosis and epidural fibrosis.

Following any surgical incision, the wound healing process results in the formation of scar tissue. While scar tissue is essential for the healing process it can have adverse effects in recovery and can result in tissue adhesions, which can lead to significant patient morbidity such as chronic pain and difficult, complicated subsequent surgeries. Management of post-surgical tissue adhesion remains suboptimal as current treatment strategies, such as adhesive barriers, do not sufficiently address patient needs. Adhesive barriers can be difficult to deliver in cases where there are small incisions or openings, such as laparoscopic surgery or injections, and can have severe side effects.

Tissue adhesion can occur through the actions of fibroblasts and fibrosis. In response to tissue injury from surgery, there may be an inflammatory-like response that releases histamines, cytokines and growth factors and promotes fibroblast migration from underlying tissues. These fibroblasts can infiltrate other tissues and deposit extracellular matrix, leading to tissue adhesion. Adhesive barriers can be used to reduce or limit such fibroblast infiltration and/or other tissue adhesion.

Kang et al. previously investigated the resorption of a 2% HA to 7% MC gel in vivo (Kang et al. *A New Paradigm for Local and Sustained Release of Therapeutic Molecules to the Injured Spinal Cord for Neuroprotection and Tissue Repair*, TISSUE ENGINEERING: Part A Volume 14, No. 3, 2009). Briefly, HA was conjugated to a BODIPY-Fluoresceint (BODIPY-FL) hydrazide and MC was conjugated to Texas Red hydrazide for visualization within the intrathecal (IT) space in rats. HA was found to degrade quickly, exhibiting a ~95% loss in fluorescent area after 24 h. In contrast, MC showed an initial degradation of ~65% after 24 h and then continued to persist within the IT space for at least 4 days. After 7 days, traces of neither HA nor MC could be detected. In view of this result, the ability of hydrogels having certain concentrations of HAMC as identified in the examples to limit fibrosis over a number of weeks in vivo was both surprising and unexpected.

In one embodiment, there is provided a hydrogel composition for reducing or limiting tissue adhesion. In various embodiments, a single administered dose of a hydrogel composition as described herein limits tissue adhesion or fibrosis for a period of greater than or equal to 1 week, 2 weeks, 3 weeks, 4 weeks, 5 weeks, 6 weeks, 7 weeks or 8 weeks.

While the composition may be administered in a single dose, in other embodiments, multiple doses may be administered.

As used herein, in one embodiment, reducing or limiting tissue adhesion means there is less adhesion when compositions as provided herein are administered to a tissue than in the absence of the hydrogel composition under standard techniques for evaluating tissue adhesion.

Hyaluronic acid (or hyaluronan) $(HA)_{[MC1]}$ is a linear polysaccharide composed of repeating disaccharide units of N-acetyl-glucosamine and D-glucuronic acid. HA is degraded enzymatically by hyaluronidase, which can be produced by cells. Its polymeric chains, of lengths of 10-15 thousand disaccharides, form random coils with large spheroidal hydrated volumes of up to 400-500 nm in diameter. Reactions can occur at the carboxyl group or the hydroxyl group of HA and also at the amino group when the N-acetyl group is removed. In one embodiment, the sodium salt of hyaluronate is used.

Pharmaceutical grade HA is available in a wide variety of molecular weights, in the range of between about 100,000 and about 3,000,000 g/mol. In one embodiment the composition comprises HA in the range of 500,000 and 2,500,000 g/mol, in one embodiment in the range of 1,000,000 and 2,000,000 g/mol, and in a preferred embodiment in the range of 1,400,000 to 1,600,000 g/mol.

Blends of unmodified HA with a gelling polymer are injectable upon an application of force to a syringe because the shear-thinning properties of HA cause the polymer chains to straighten and align themselves, permitting flow through the needle. HA then returns to its high viscosity, zero shear structure upon exiting the needle as the polymeric chains once again become entangled amongst themselves.

The other polymer component of the hydrogel is methylcellulose (MC). MC is an example of a temperature sensitive gel, or a thermally reversible gel, that gels upon increase in temperature. When the degree of substitution of hydroxyl groups with methyl groups is between 1.4 and 1.9 per monomer unit, MC has inverse thermal gelling properties whereby it gels upon an increase of temperature. As the temperature increases, the methyl groups of MC form hydrophobic interactions and water molecules are released from interacting with MC, thereby forming a gel.

The MC may have a molecular weight in the range of between about 2,000 and about 1,000,000 g/mol. In one embodiment the composition comprises MC in the range of 10,000 and 500,000 g/mol, in one embodiment in the range of 100,000 to 400,000 g/mol, and in one embodiment in the range of 200,000 to 300,000 g/mol.

Hydrogel compositions as described herein may suitably be prepared through the physical blending of HA and MC in a buffer, for example, phosphate buffered saline (PBS). The compositions may be sterilized by autoclave, gamma sterilization or filter sterilization.

Many surgeries occur through small openings or incisions, such as laparoscopic surgeries or biopsies. Adhesive barriers that can be applied through such small openings or incisions, such as by injection, can more easily be delivered to reduce or limit tissue adhesion in these surgeries than non-injectable anti-adhesive barriers.

In one embodiment, the composition is injectable.

The hydrogel compositions described herein are injectable, wherein the injection may be, for example, by syringe, via a catheter or other device for delivering a liquid material across the skin such as by microjet. Alternatively, the composition may be administered by injection by ejecting the material from a syringe without a needle, topically, or into an open wound in some embodiments. When administered via injection, the composition can operate as a depot injection, the composition forming a localized mass. In one embodiment the composition is administered by a single injection. The hydrogel compositions as described herein may be administered in a number of ways depending upon the area to be treated. Without limiting the generality of the foregoing, in a particular embodiment, the compositions are administered by subcutaneous, intradermal or intramuscular injection.

In one embodiment, the hydrogel composition is administrable with a 10-30 gauge needle, in one embodiment, a 20-25 gauge needle, in one embodiment, without a needle.

The hydrogel compositions described herein may be combined with any pharmaceutically acceptable carrier or excipient. As used herein, a "pharmaceutically acceptable carrier" or "excipient" can be a pharmaceutically acceptable solvent, suspending agent or any other pharmacologically inert vehicle selected to facilitated delivery of the hydrogel composition to a subject. The excipient may be liquid or solid and is selected, with the planned manner of administration in mind, so as to provide for the desired consistency, etc., when combined with the other components of the hydrogel composition. Examples of pharmaceutically acceptable carriers include one or more of water, saline, phosphate buffered saline, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the pharmacological agent.

In some embodiments, the pharmaceutically acceptable carrier is phosphate buffered saline or saline.

One type of fibrosis is epidural fibrosis. Epidural fibrosis is a non-physiologic scar usually formed at the site of neurosurgical exposure of the spinal dura mater. Limiting epidural fibrosis is important in reducing failed back surgery syndrome (FBSS). FBSS occurs when the fibrotic tissue adheres to the dura mater and results in pain. Reoperations to relieve pain after FBSS are expensive and do not always result in complete pain relief, resulting in long term pain, lost wages and a decrease in quality of life. In addition to the pain implications of epidural fibrosis there is a secondary problem where the fibrotic tissue increases complications with subsequent surgeries that may have to be carried out due to unrelated issues. For example, if a spinal fusion is carried out and years later an unrelated disc surgery is required, the scar tissue from the original spinal fusion has to be removed first before any additional surgeries can be carried out. During the removal of existing scar tissue there is an increased risk of a dural tear. There is no routine procedure available to limit epidural fibrosis.

In one embodiment, there is provided a method of reducing or limiting laminectomy and/or dural fibrosis, comprising administering a composition as described herein to a tissue in an amount effective to limit or reduce tissue adhesion. In one embodiment, the tissue is a tissue of the central nervous system, in another embodiment the tissue is a tissue of the abdominal cavity, and in another embodiment, the tissue is a tissue of a joint. In one embodiment, the composition is administered to the spinal cord.

As used herein, "effective amount" refers to an amount effective, at concentrations and for a particular period of time necessary, to achieve the desired result. An effective amount of the hydrogel composition may vary according to factors such as the surgery, disease state, age, sex, and weight of the individual, and the ability of the hydrogel composition to elicit a desired response in the individual. An effective amount is also one in which any detrimental effects of the hydrogel composition are outweighed by the beneficial effects.

As used herein "subject" refers to an animal being administered a hydrogel composition, in one embodiment a mammal, in one embodiment a human patient. As used herein "treatment" and grammatical variations thereof refers to administering a compound or composition of the present invention, in one embodiment in order to reduce or limit tissue adhesion. The treatment may require administration of multiple doses, which may be at regular intervals.

The hydrogel composition as described herein may conveniently be presented in unit dosage form of a single-use syringe that has been sterilized for injection with or without a needle, in some embodiments.

In one embodiment, there is provided a method of reducing or limiting adhesion comprising administering, preferably by injection, an effective amount of a hydrogel composition as described herein.

Without limiting the generality of the foregoing, the present compositions have particular utility in association with surgeries involving small incisions or openings. Other uses include the treatment of tissue adhesion in cataract removal surgery, caesarean section, joint replacement or repair, hysterectomy, or dental surgery.

All documents referenced herein are incorporated by reference, however, it should be appreciated that any patent, publication, or other disclosure material, in whole or in part, that is incorporated by reference herein is incorporated only to the extent that the incorporated material does not conflict with definitions, statements, or other disclosure material set forth in this disclosure. As such, and to the extent necessary, the disclosure as explicitly set forth herein supersedes any conflicting material incorporated herein by reference.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

The embodiments of the invention described above are intended to be exemplary only. The scope of the invention is therefore intended to be limited solely by the scope of the appended claims.

EXAMPLES

Example 1—Preparation and Sterilization of HAMC Gels

Preparation of HAMC Gel
4.2:9 w/w HAMC was prepared as follows (per mL of gel made):

| | |
|---|---|
| 42 mg | Sodium Hyaluronate |
| 90 mg | Methylcellulose |
| 868 µL | Phosphate Buffered Saline |

HAMC hydrogels were prepared through the physical blending of sterile hyaluronan and methylcellulose in phosphate buffered saline (PBS), (speed mixing at maximum speed for 30 seconds, centrifuge at 5000 RPM for 1 minute). MC and HA were allowed to dissolve overnight at 4° C. Gels were kept at 4° C. until sterilization.

Example 2—Fibrosis Comparison of HAMC Compositions

The level of dural fibrosis and laminectomy fibrosis were measured in rats treated with six different HAMC compositions.

Rat Laminectomy and Surgery

Adult female rats were anesthetized by inhalation of 2% isoflurane and oxygen. The rats underwent a laminectomy at L5-L6 in order to expose the dura. Following the laminectomy, 50 µL of either HAMC compositions with wt % HA:wt % MC of: 0:0.75, 0.7:1.5, 1.4:3, 2.8:6, 4.2:9, or 5.6:12, or aCSF were applied to the exposed dura.

The wound was closed and the rats were allowed to recover. Buprenorphine (0.05 mg/kg) was administered to the rats for pain control before awakening, then every 12 hours for 48 hours. Rats were kept in a cage in a temperature controlled room with a 12 hour light/dark cycle.

Tissue Processing and Histological Analysis

Figure 2:
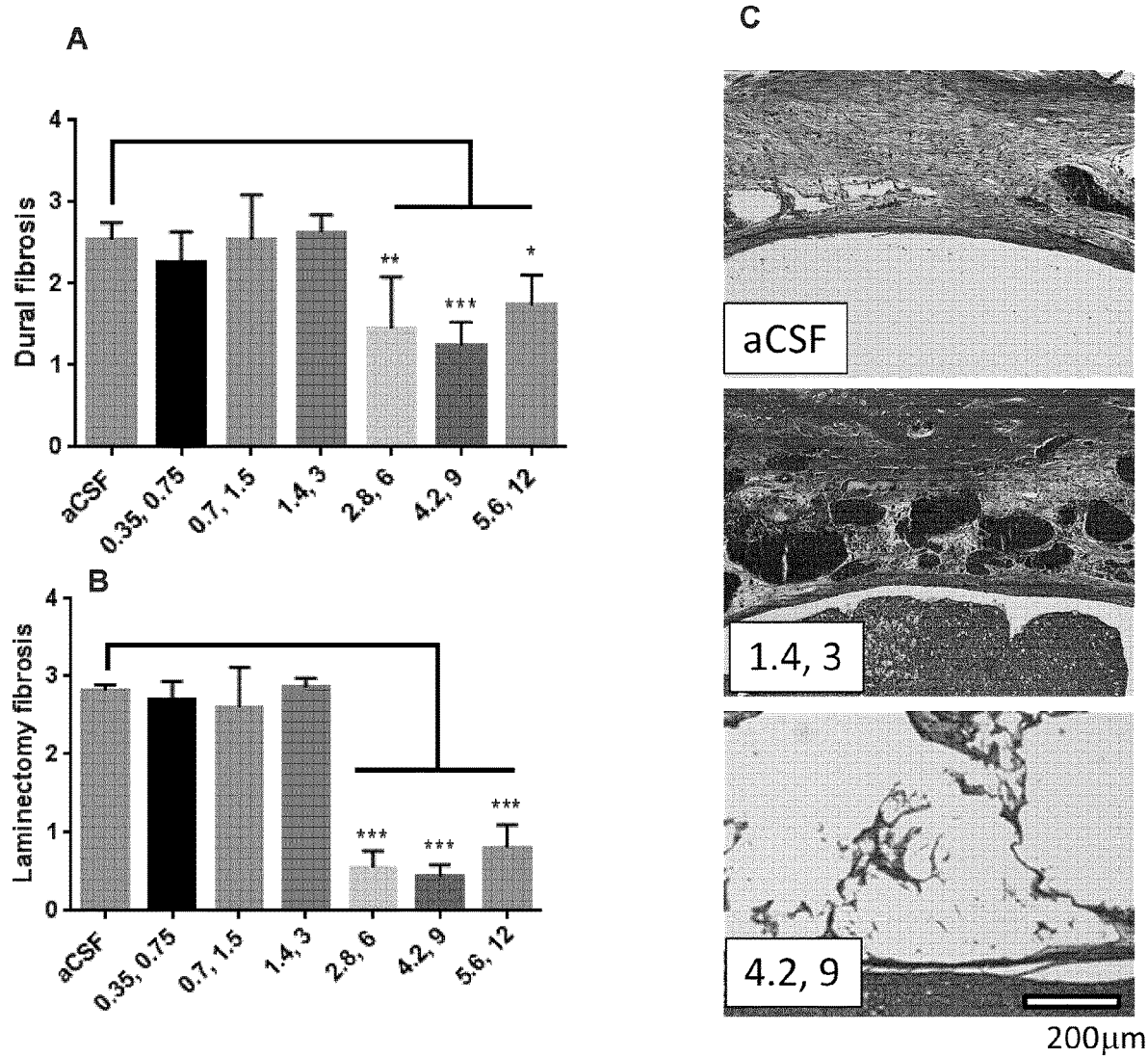
FIG. 2A shows the level of dural fibrosis in a rat model with L5-L6 laminectomy after 3 weeks with the following applied to the dura after the laminectomy: artificial cerebrospinal fluid (aCSF) or formulations of HAMC at wt % HA:wt % MC of: 0.35:0.75, 0.7:1.5, 1.4:3, 2.8:6, 4.2:9, or 5.6:12.
FIG. 2B shows the level of laminectomy fibrosis in a rat model with L5-L6 laminectomy after 3 weeks with the following applied to the dura after the laminectomy: aCSF or formulations of HAMC at wt % HA:wt % MC of: 0.35:0.75, 0.7:1.5, 1.4:3, 2.8:6, 4.2:9, or 5.6:12.
FIG. 2C shows representative examples of the level of dural fibrosis and laminectomy fibrosis in a rat model with L5-L6 laminectomy after 3 weeks with the following applied to the dura after the laminectomy: aCSF or formulations of HAMC at wt % HA:wt % MC of 1.4:3 or 4.2:9.

The rats were sacrificed 3 weeks post-laminectomy. Tissue was removed en bloc, decalcified using formic acid and embedded in paraffin. Tissue was sectioned to 8 µm and stained with Masson's trichrome. A scoring scale of 0-3 was developed whereby 0 was equivalent to no fibrosis and 3 was equivalent to severe fibrosis. In a blinded histological analysis, a representative sample of sections was evaluated for each treatment on the 0-3 scale. Unexpectedly, rats treated with HAMC compositions with wt % HA:wt % MC of 2.8:6, 4.2:9, or 5.6:12 showed significantly reduced levels of fibrosis when compared with rats treated with aCSF (FIG. 2).

Example 3—Fibrosis Comparison of 4.2:9 HAMC with Oxiplex® Adhesion Barrier

To determine the performance of the 4.2:9 HAMC composition, the level of dural fibrosis and laminectomy fibrosis were compared in rats treated with aCSF, Oxiplex®, or 4.2:9 HAMC.

Rat Laminectomy and Surgery

Adult female rats were anesthetized by inhalation of 2% isoflurane and oxygen. The rats underwent a laminectomy at L5-L6 in order to expose the dura. Following the laminectomy, 50 µL of either aCSF, Oxiplex®, or a HAMC composition with wt % HA:wt % MC of 4.2:9 were applied to the exposed dura.

The wound was closed and the rats were allowed to recover. Buprenorphine (0.05 mg/kg) was administered to the rats for pain control before awakening, then every 12 hours for 48 hours. Rats were kept in a cage in a temperature controlled room with a 12 hour light/dark cycle.

Tissue Processing and Histological Analysis

Figure 3:
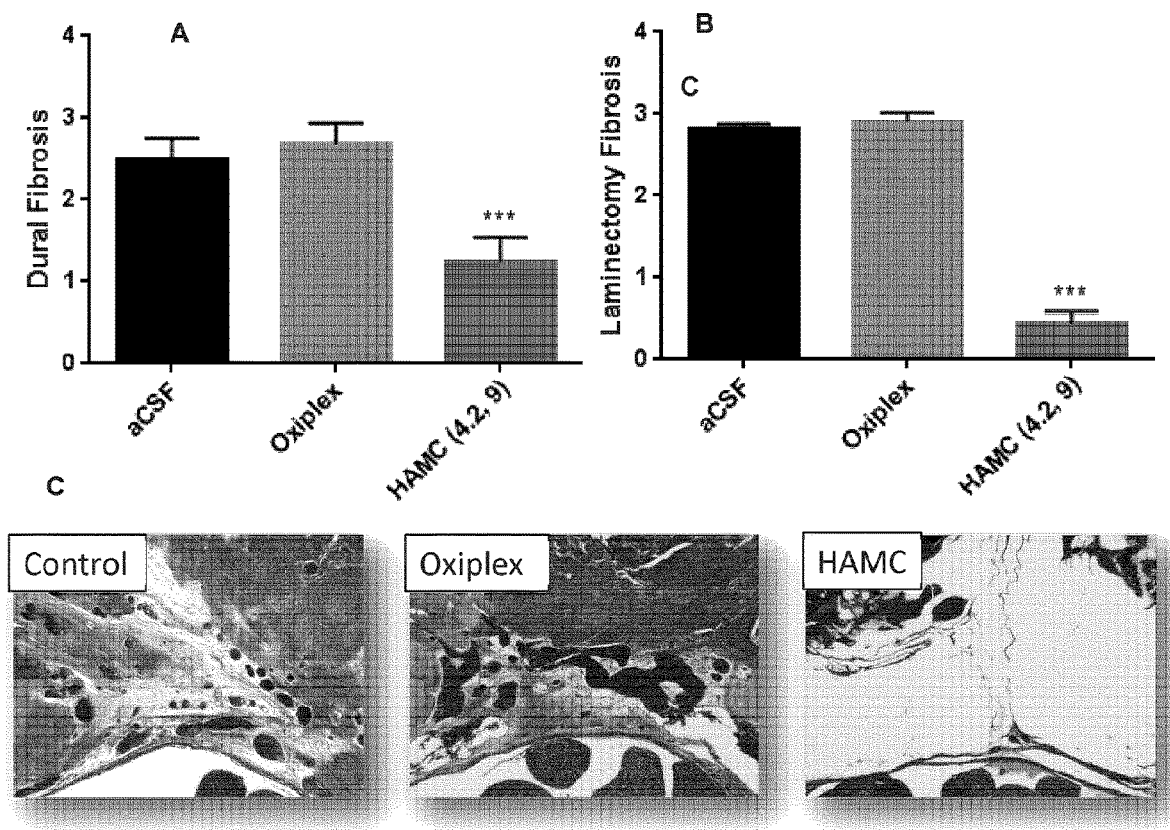
FIG. 3A shows the level of dural fibrosis in a rat model with L5-L6 laminectomy after 3 weeks with the following applied to the dura after the laminectomy: aCSF, Oxiplex® a, or a formulation of HAMC at a wt % HA:wt % MC of 4.2:9.
FIG. 3B shows the level of laminectomy fibrosis in a rat model with L5-L6 laminectomy after 3 weeks with the following applied to the dura after the laminectomy: aCSF, Oxiplex®, or a formulation of HAMC at a wt % HA:wt % MC of 4.2:9.
FIG. 3C shows representative examples of the level of dural fibrosis and laminectomy fibrosis in a rat model with L5-L6 laminectomy after 3 weeks with the following applied to the dura after the laminectomy: aCSF, Oxiplex®, or a formulation of HAMC at a wt % HA:wt % MC of 4.2:9.

The rats were sacrificed 3 weeks post-laminectomy. Tissue was removed en bloc, decalcified using formic acid and embedded in paraffin. Tissue was sectioned to 8 µm and stained with Masson's trichrome. A scoring scale of 0-3 was developed whereby 0 was equivalent to no fibrosis and 3 was equivalent to severe fibrosis. In a blinded histological analysis, a representative sample of sections was evaluated for each treatment group on the 0-3 scale. Rats treated with a HAMC compositions with wt % HA:wt % MC of 4.2:9 showed significantly reduced levels of fibrosis when compared with either aCSF or Oxiplex® (FIG. 3).

What is claimed is:

1. A method of reducing or limiting tissue adhesion comprising
    contacting the tissue with an effective amount of a hydrogel composition comprising:
        2% to 6% by weight hyaluronan, and
        3% to 18% by weight methylcellulose,
    wherein the combined total amount of hyaluronan and methylcellulose in the hydrogel is between 8 and 24% by weight;
    and wherein the ratio of hyaluronan:methylcellulose is between 1:1 and 1:5 w/w.

2. The method of claim 1, wherein the combined total amount of hyaluronan and methylcellulose in the hydrogel is between 10 and 16%.

3. The method of claim 1, wherein the hydrogel comprises between 3 and 5% by weight hyaluronan.

4. The method of claim 1, wherein the hydrogel comprises between 8 and 10% by weight methylcellulose.

5. The method of claim 1, wherein the ratio of hyaluronan:methylcellulose is between 1:1.5 and 1:3 w/w.

6. The method of claim 5, wherein the ratio of hyaluronan:methylcellulose is 1:2.14.

7. The method of claim 1, wherein the hyaluronan has a molecular weight between 100,000 g/mol and 3,000,000 g/mol and the methylcellulose has a molecular weight between 10,000 g/mol and 500,000 g/mol.

8. The method of claim 1, wherein the hydrogel composition is injectable.

9. The method of claim 1, wherein the tissue is a tissue of the central nervous system, abdominal cavity, or joint.

10. The method of claim 1, wherein the hydrogel composition is administered to a patient during surgery or perioperatively.

11. The method of claim 10, wherein the surgery is laparoscopic surgery.

12. The method of claim 10, wherein the surgery comprises spinal surgery, disc repair surgery, cataract removal surgery, caesarean section, joint replacement or repair, hysterectomy, or dental surgery.

13. The method of claim 1, wherein the tissue adhesion comprises fibrosis.

14. The method of claim 13, wherein the fibrosis comprises dural fibrosis.

15. The method of claim 13 wherein the fibrosis comprises laminectomy fibrosis.

16. The method of claim 1, wherein the effective amount is between 1 and 100 mL.

17. The method of claim 1, wherein the tissue adhesion is limited for a period of greater than or equal to 1 week, 2 weeks, 3 weeks, 4 weeks, 5 weeks, 6 weeks, 7 weeks or 8 weeks.

18. The method of claim 1, wherein the remainder of the hydrogel composition is water and biocompatible buffers and/or salts.

* * * * *